United States Patent
Massholder et al.

(10) Patent No.: US 6,343,400 B1
(45) Date of Patent: Feb. 5, 2002

(54) CLEANING SYSTEM USING ULTRAVIOLET RADIATION AND PHOTOACTIVATABLE SEMICONDUCTOR MATERIAL

(75) Inventors: Karl Massholder, Panoramaweg 27, D-69250 Schoenau (DE); Peter Manschott, Schoenau (DE)

(73) Assignee: Karl Massholder, Schoenau (DE)

( * ) Notice: Subject to any disclaimer, the term of this patent is extended or adjusted under 35 U.S.C. 154(b) by 0 days.

(21) Appl. No.: 09/331,652

(22) PCT Filed: Dec. 23, 1997

(86) PCT No.: PCT/EP97/07254
§ 371 Date: Feb. 14, 2000
§ 102(e) Date: Feb. 14, 2000

(87) PCT Pub. No.: WO98/27891
PCT Pub. Date: Jul. 2, 1998

(30) Foreign Application Priority Data

Dec. 23, 1996 (DE) .......................... 196 54 108

(51) Int. Cl.[7] .............................................. A46B 15/00
(52) U.S. Cl. .............................. 15/105; 15/167.1; 134/1
(58) Field of Search ....................... 15/22.1, 105, 167.1; 433/29; 607/79; 134/1; 250/504 H

(56) References Cited

U.S. PATENT DOCUMENTS

| 2,397,757 A | * | 4/1946 | Schwedersky | 15/105 |
| 2,688,971 A | * | 9/1954 | Daniels et al. | 15/105 |
| 3,261,978 A | * | 7/1966 | Brenman | 15/105 |
| 3,667,454 A | * | 6/1972 | Prince | 15/105 |
| 4,779,173 A | * | 10/1988 | Carr et al. | 15/105 |
| 4,983,379 A | | 1/1991 | Schaeffer | 424/52 |
| 5,030,090 A | * | 7/1991 | Maeda et al. | 433/29 |
| 5,160,194 A | * | 11/1992 | Feldman | 15/167.1 |
| 5,306,143 A | * | 4/1994 | Levy | 15/167.1 |
| 6,094,767 A | * | 8/2000 | Iimura | 15/105 |

FOREIGN PATENT DOCUMENTS

| EP | 0 743 029 | | 11/1996 | | |
| JP | 60011411 A | * | 1/1985 | | |
| JP | 3-251207 A | * | 11/1991 | | 15/105 |
| JP | 6-113920 A | * | 4/1994 | | 15/167.1 |
| WO | WO 92 06671 | | 4/1992 | | |

* cited by examiner

Primary Examiner—Robert J. Warden, Sr.
Assistant Examiner—Theresa T. Shider
(74) Attorney, Agent, or Firm—Foley & Lardner

(57) ABSTRACT

A cleaning system for cleaning a surface is proposed, the cleaning system having:
  a cleaning tool (2) with a working region (A) and with a UV-light source (7), the UV-radiation of which emerges from the tool (2) in the working region (A), and
  a cleaning agent which contains a photoactivatable semiconductor material (3), UV-radiation being fed directly into the photoactivatable semiconductor material (2) in the working region (A) via a light guide device (9, 14).

12 Claims, 1 Drawing Sheet

CLEANING SYSTEM USING ULTRAVIOLET RADIATION AND PHOTOACTIVATABLE SEMICONDUCTOR MATERIAL

BACKGROUND OF THE INVENTION

The invention relates to a cleaning system and to a method for cleaning a surface.

Hygiene plays an important part in many areas of daily life. Good hygiene can contribute to preventing many illnesses by removing or destroying germs which settle on surfaces. Cleanliness is another aspect. When surfaces are cleaned, visually disturbing impurities are removed, so that a more agreeable external appearance is obtained. It is also sometimes necessary to remove deposits or accumulated substances which have occurred due to environmental pollution.

Previous cleaning methods have been based, as a rule, on cleaning off the surface mechanically, that is to say a cleaning tool is led over the surface and, at the same time, impurities are released and stripped off mechanically. Chemical agents are often used to destroy or kill germs and bacteria, but then have to be removed again themselves and occasionally exhibit aggressive behavior toward the surface to be cleaned. In many instances, therefore, great care must be taken in the choice of cleaning or scouring agents, and these must be appropriately adjusted to the surface to be cleaned. However, particularly in the control of germs and bacteria, it is to be observed that specific germs develop increasing resistance to specific agents which are used to control them. Even after cleaning has been carried out, the desired lack of germs or even freedom from germs is then not achieved, although this is not noticed immediately at all.

SUMMARY OF THE INVENTION

The object on which the invention is based is to specify a cleaning system which makes it possible to simplify the cleaning of surfaces, to increase the reliability of the cleaning effect and largely to rule out secondary effects. The object of the invention is, furthermore, to specify an improved method for cleaning a surface.

The solution proceeds from a cleaning system for cleaning a surface, said cleaning system having:

a cleaning tool (2) with a working region (A) and with a UV-light source (7), the UV-radiation of which emerges from the tool (2) in the working region (A), and a cleaning agent which contains a photoactivatable semiconductor material (3).

BRIEF DESCRIPTION OF THE DRAWINGS

The single FIGURE shows a diagrammatic illustration of the cleaning system with a toothbrush.

DETAILED DESCRIPTION OF PREFERRED EMBODIMENTS

Figure 1:
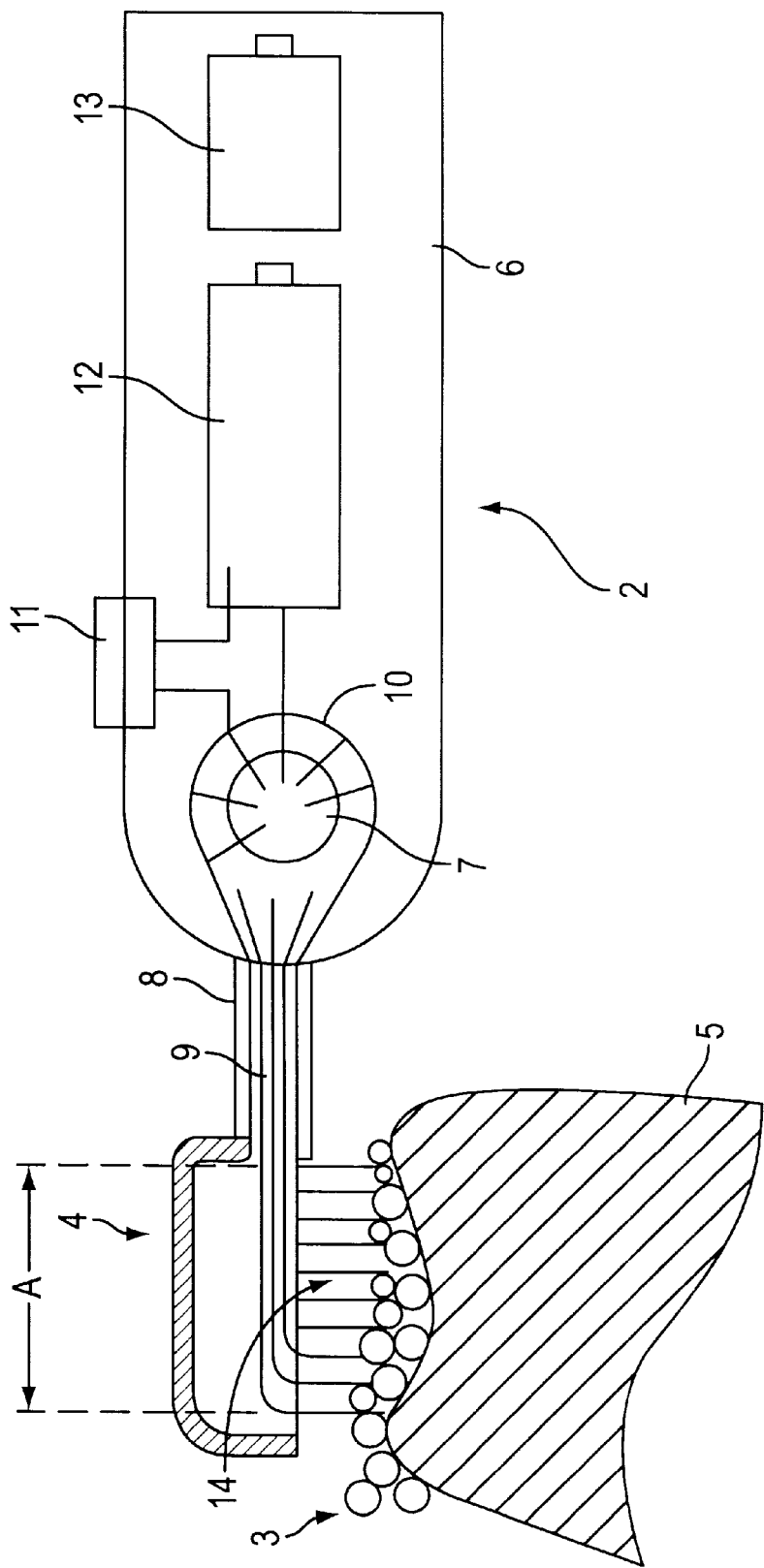

The cleaning system according to the invention is then defined by a light guide device (9, 14), via which UV-radiation is fed directly into the photo-activatable semiconductor material (3) in the working region (A).

The cleaning system according to the invention is thus designed in such a way that UV-light from a UV-light source is fed directly into the photoactivatable semiconductor material in the working region of the cleaning tool by a light guide device. Increased effectiveness of the cleaning effect and substantial avoidance of secondary effects are thereby achieved.

There is no question of putting humans at risk from UV-radiation. The UV-radiation is guided directly to the surface to be cleaned and only there emerges from the light guide. Furthermore, the UV-radiation is concentrated onto small regions of the surface area, so that the energy necessary for generating the UV-radiation is utilized efficiently.

The procedure for using the cleaning system according to the invention in order to clean a surface is extremely simple:

It is sufficient, initially, to apply a photoactivatable semiconductor, for example in powder form or in the form of a suspension or liquid, onto the surface to be cleaned. It is then necessary merely to ensure that UV-radiation passes via a light guide directly onto the surface. Although the processes have not yet been finally explained, it is assumed that the UV-radiation then activates the semiconductor, that is to say brings about a change in the electron configuration of the semiconductor molecules. Photo-activation means that electrons are raised from the valence band into the conduction band as a result of the absorption of light in the semiconductor, for example n-$TiO_2$. This gives rise to a redox potential which, as a result of the formation of radical species or mechanisms, causes microorganisms to be killed. Since these processes are unspecific, oxidative degradative reactions also occur at the same time. Since the semiconductor does not change, it is referred to as a catalyst. This method can therefore be used with excellent results for disinfection. It may also be used, however, to oxidize oxidizable substances, for example hydrocarbons. Thus, for example, oil stains can be removed by scattering the photoactivatable semi-conductor in powder form and then causing UV-light, either from the sun or a UV-light source, to act on it. The oil is oxidized and then decomposes largely into carbon dioxide and water.

A mechanical cleaning instrument is preferably used in this case as a light guide for the UV-radiation. In addition to the oxidation of the impurities or germs, a tool is then available at the same time, by means of which these oxidized impurities or germs can be stripped off mechanically. The advantages of conventional cleaning are therefore combined, here, with the advantages of "oxidative" cleaning. The cleaning times can thereby be kept short.

A brush, in which at least some bristles are designed as optical fibers, is preferably used as a cleaning instrument. In this embodiment, just as with conventional brushes, the bristles serve as mechanical cleaning tools. In addition, however, the bristles, or at least some bristles, also serve for guiding the UV-light onto the surface, where it is used, together with a photoactivatable semiconductor, for oxidative cleaning. The combination of mechanical cleaning with the oxidation of the dirt to be controlled increases the effect of a conventional brush, particularly with regard to the control of germs.

Moreover, this embodiment also has the advantage that, when cleaning is being carried out, the bristles displace the semiconductor repeatedly from one point to another, so as to ensure, with a high degree of probability, that all the germs or all the dirt on the surface can be covered and oxidized.

The brush is designed in a particularly advantageous way as a toothbrush, the UV-light source being arranged in the handle of the toothbrush. This results in a very small overall size, so that the toothbrush does not exceed the overall size of a toothbrush existing hitherto. The electrical components, which are necessary, as a rule, for generating the UV-radiation, and water-carrying parts on the toothbrush are reliably separated. The interior of the handle can be designed to be waterproof without difficulty, if the UV-radiation is led into the bristle zone by means of a light guide. Cleaning habits do not have to be changed virtually at all, as compared with a conventional toothbrush. Bacteria on teeth and gums, and, above all, also in tooth gaps are destroyed, even when the bristles do not penetrate directly into the tooth gaps. A positive side effect has proved to be that the teeth become white without any chemical aids. It is obvious, therefore, that, in addition to the germs, other organic impurities, which inter alia discolor the teeth, are also removed oxidatively. It is therefore, possible, for example, to put together, especially for smokers, a suitable system with "smoker's toothpaste" and a toothbrush. The dirt is also stripped off mechanically as a result of the abrasive effect of the cleaning bodies made of semi-conductor material.

The semiconductor material is preferably used in the form of cleaning bodies or together with cleaning bodies. It therefore not only assists the oxidation of the impurities or the dirt to be removed, but also contributes to mechanical cleaning.

The semiconductor material is preferably used in pasty form or as an ingredient of a paste. The semiconductor material then adheres better to the substrate, that is to say the surface to be cleaned. This is advantageous whenever the surface is not horizontal and cleaning is carried out from above in the direction of gravity, that is to say, for example, in the case of walls which are vertical or are at some inclination, or in the case of ceilings or other surfaces which overhang.

In an alternative embodiment, the semiconductor material may be designed as a floating body or be bound to a floating body. It is then consequently also possible to clean surfaces to which access for mechanical cleaning has hitherto been difficult, specifically the surfaces of liquids, for example of lakes, rivers or oceans. Oil stains often occur on water surfaces, whether due to defective boats or ships or due to the deliberate or negligent emptying of oil residues into the water. It is possible for these oil stains to be removed mechanically only with great difficulty and at a high outlay. If the semiconductor material is designed to be floatable, the catalytic effect of the semiconductor material, which occurs under the action of the UV-light contained in sunlight, can then be used to degrade dirt of this kind oxidatively and consequently remove it.

It is particularly preferred, in this case, to use as a floating body a mineral material, an organic material or a jelly-like liquid with a specific gravity lower than 1 g/cm$^3$. For example, expanded clay, perlite, aerated concrete, lava, pumice or siliceous earth come under consideration as a mineral material. Vegetable products, for example popcorn, may be used as organic material. Jellies may be used as a liquid, which bind the semiconductor material, transmit the UV-light and nevertheless float. Floating bodies of this kind have, specifically, the advantage that they do not lead to additional environmental pollution, but instead, after the degradation of the dirt, either can be biologically degraded or sink and settle.

The UV-radiation preferably has a wavelength in the range of 280 to 400 nm, in particular in the range of 320–380 nm. This UV-radiation is contained in sunlight. It is essentially harmless to humans. It is used even for cosmetic and medical purposes. This UV-radiation can therefore be employed even when surfaces in or on the human body are to be cleaned, for example the surfaces of teeth in the mouth.

Titanium dioxide or silicon carbide is preferably used as a photoactivatable semiconductor. Both semiconductors are relatively cost-effective and are available in large quantities.

The invention is described below with reference to a preferred exemplary embodiment, in conjunction with the drawing in which: the single FIGURE shows a diagrammatic illustration of a cleaning system with a toothbrush.

A cleaning system 1 has a toothbrush 2 and a photoactivatable semiconductor material 3. The tooth-brush 2 is illustrated with its head 4 above a tooth 5, the surfaces of which are to be cleaned.

The toothbrush 2 has a handle 6, in which a UV-light source 7 is arranged. The UV-light source generates UV-radiation with a wavelength in the range of 320 to 400 nm. This UV-radiation is guided to the brush head 4 via a light guide device 9 arranged in the stem 8. A reflector 10 is additionally provided, which directs the UV-radiation into the entrance of the light guide device 9.

The UV-light source can be activated via a switch 11. The switch 11 is arranged in a current path between the UV-light source 7 and batteries 12, 13 which are likewise located in the handle 6 of the toothbrush.

The light guide device 9 has a number of light-guiding fibers which may be used at the same time as bristle material. A suitable plastic for this purpose is, for example, polyacrylamide. This plastic, on the one hand, is capable of guiding UV-light in the specified wavelength range. On the other hand, however, it is also sufficiently stable to be capable of functioning as a toothbrush bristle.

In the toothbrush head, therefore, there are one or more types of bristle: at least some bristles 14 form part of the light guide device 9. There may, in addition, also be other bristles which do not serve as light guides, but merely have the function of mechanical cleaning off.

Small cleaning bodies, which consists at least partially of a photoactivatable semiconductor material 3, for example titanium dioxide or silicon carbide, are illustrated diagrammatically on the tooth 5. Either all the small cleaning bodies may be formed in a unitary manner from the semiconductor material or the semi-conductor material may be provided in addition to other small cleaning bodies. It is, of course, also possible not to design the semiconductor material as small cleaning bodies, but to accommodate it together with the small cleaning bodies in the pasty mass of a tooth cream.

The teeth, then, can be cleaned in the conventional way. During cleaning, the UV-light source 7 is switched on by the actuation of the switch 11. In a working region identified by A, the UV-radiation then impinges onto the semiconductor material 3 which is thereby activated. Free valences occur, with the result that impurities, germs or bacteria located on the tooth surface are oxidized and consequently inactivated. The advantage of this procedure is that the teeth are cleaned even in those places which the bristles do not reach directly, for example in tooth gaps. As a rule, however, the semiconductor material 3 is also flushed into such spaces by means of the liquid which is present or is generated in the mouth when the teeth are being cleaned. As long as the UV-radiation reaches these parts, cleaning by oxidation takes place there.

During cleaning, the layer of tooth cream in which the semiconductor material 3 is contained is very highly diluted, at least locally, so that the semi-conductor material 3, always activated with exceptionally high statistical probability, reaches the surface of the tooth 5 and the cleaning effect by oxidation can be exercised there.

Other surfaces may, of course, also be cleaned in the same way, if an appropriate cleaning agent, which contains the photoactivatable semiconductor material and a correspondingly designed brush, is used. Instead of a brush, a scraper may also be used, if care is taken to ensure that the UV-light can emerge at its scraping edge or at least in the immediate vicinity and can strike the surface to be cleaned.

What is claimed is:

1. A cleaning system for cleaning a surface, said cleaning system comprising:

a cleaning tool with a working region containing bristles, a radiation source and a light guide device via which radiation is fed from the radiation source to a position located in the working region where the radiation emerges from the cleaning tool, and a cleaning agent wherein the radiation source is a UV-radiation source, the cleaning agent contains a photoactivatable semiconductor material, and the UV radiation is fed directly into the photoactivatable semiconductor material at the position located in the working region.

2. The cleaning system as claimed in claim 1, wherein a the mechanical cleaning tool is used as the light guide device for the UV-radiation.

3. The cleaning system as claimed in claim 2, wherein at least some bristles are designed as optical fibers.

4. The cleaning system as claimed in claim 3, wherein the cleaning tool is a toothbrush, and the UV-light source is arranged in the handle of the toothbrush.

5. The cleaning system as claimed in claim 1, wherein the semiconductor material is used in the form of cleaning bodies or together with cleaning bodies.

6. The cleaning system as claimed in claim 1, wherein the semiconductor material is in pasty form or as an ingredient of a paste.

7. The cleaning system as claimed in claim 1, wherein the semiconductor material is bound to floating bodies or designed as floating bodies.

8. The cleaning system as claimed in claim 7, wherein a mineral material, an organic material or a jelly-like liquid with, a specific gravity lower than 1 $g/cm^3$ is used as the floating body.

9. The cleaning system as claimed in claim 1, wherein the photoactivatable semiconductor material is selected from the group consisting of titanium dioxide or silicon carbide or mixtures thereof.

10. The cleaning system as claimed in claim 1, wherein the radiation of the UV-light source has a wavelength in the range of 280 nm–400 nm.

11. A method for cleaning a surface comprising: contacting the cleaning system as claimed in claim 1 with a surface in need of cleaning; and activating the UV-radiation source to activate the photoactivatable semiconductor material for a time sufficient to clean the surface.

12. The cleaning system as claimed in claim 1, wherein the radiation of the UV light source has a wavelength in the range of 320–380 nm.

* * * * *